United States Patent
Kieturakis (10) Patent No.: US 6,387,056 B1
(45) Date of Patent: May 14, 2002

(54) EXCISIONAL BIOPSY NEEDLE AND METHOD FOR USE WITH IMAGE-DIRECTED TECHNOLOGY

(76) Inventor: Maciej J. Kieturakis, 372 Beverly Dr., San Carlos, CA (US) 94070

(*) Notice: Subject to any disclaimer, the term of this patent is extended or adjusted under 35 U.S.C. 154(b) by 0 days.

(21) Appl. No.: 09/347,107

(22) Filed: Jul. 2, 1999

Related U.S. Application Data (63) Continuation of application No. 09/035,728, filed on Mar. 5, 1998, now abandoned, which is a division of application No. 08/696,557, filed on Aug. 14, 1996, now Pat. No. 5,794,626, which is a continuation of application No. 08/292,479, filed on Aug. 18, 1994, now abandoned.

(51) Int. Cl.[7] .................................................. A61B 5/00
(52) U.S. Cl. ........................................................ 600/565
(58) Field of Search ................................. 600/564–568; 606/167, 170

(56) References Cited

U.S. PATENT DOCUMENTS

| | | | |
|---|---|---|---|
| 4,191,191 A | 3/1980 | Auburn | 128/347 |
| 4,338,952 A | 7/1982 | Augros | 128/757 |
| 4,535,773 A | 8/1985 | Yoon | 604/51 |
| 4,601,710 A | 7/1986 | Moll | 604/165 |
| 4,654,030 A | 3/1987 | Moll et al. | 604/165 |
| 4,681,123 A * | 7/1987 | Valtchev | 600/566 |
| 4,702,260 A * | 10/1987 | Wang | 600/564 |
| 5,030,201 A | 7/1991 | Palestrant | 604/22 |
| 5,069,679 A | 12/1991 | Taheri | 606/159 |
| 5,116,353 A | 5/1992 | Green | 606/184 |
| 5,147,316 A | 9/1992 | Castillenti | 604/164 |
| 5,147,376 A | 9/1992 | Pianetti | 606/170 |
| 5,203,773 A | 4/1993 | Green | 604/104 |
| 5,209,736 A | 5/1993 | Stephens et al. | 604/164 |
| 5,224,488 A | 7/1993 | Neuffer | 128/751 |
| 5,224,952 A | 7/1993 | Deniega et al. | 606/184 |
| 5,226,890 A | 7/1993 | Ianniruberto et al. | 604/164 |
| 5,232,451 A | 8/1993 | Frietas et al. | 606/174 |
| 5,258,003 A | 11/1993 | Ciaglia et al. | 606/185 |
| 5,271,380 A | 12/1993 | Riek et al. | 128/4 |
| 5,279,567 A | 1/1994 | Ciaglia et al. | 604/117 |
| 5,318,040 A | 6/1994 | Kensey et al. | 128/754 |
| 5,399,167 A * | 3/1995 | Deniega | 600/567 |

FOREIGN PATENT DOCUMENTS

| | | | |
|---|---|---|---|
| SU | 1551-362 | * | 3/1990 |
| SU | 168108 | * | 9/1991 |

* cited by examiner

Primary Examiner—Max Hindenburg
(74) Attorney, Agent, or Firm—Skjerven Morrill MacPherson LLP; Norman R. Klivans (57) ABSTRACT

An excisional biopsy needle assembly for use in combination with a stereotactic platform for excising tissue from the interior of the body. The biopsy needle includes a rotatable flexible blade that is capable of transforming between a contracted configuration for piercing into the interior of the body and an expanded configuration in which the flexible blade is expanded relative to the shaft of the needle for excising tissue. The needle assembly may be mounted in a stereotactic needle for a breast biopsy procedure that digitally directs the needle tip into a lesion with the flexible blades in a contracted configuration, then expands the flexible blades to the expanded configuration and rotates the blades thus excising tissue in a region having a cross sectional dimension that is large in relation to the cross section of the needle shaft. The excised tissue is extracted from the needle tip through an aspiration channel.

8 Claims, 6 Drawing Sheets

EXCISIONAL BIOPSY NEEDLE AND METHOD FOR USE WITH IMAGE-DIRECTED TECHNOLOGY

This application is a continuation application of Ser. No. 09/035,728, filed Mar. 5, 1998, now abandoned which is a divisional application of Ser. No. 08/696,557, filed Aug. 14, 1996, now U.S. Pat. No. 5,794,626 issued Aug. 18, 1998, which is a continuation of Ser. No. 08/292,479, filed Aug. 18, 1994, now abandoned.

BACKGROUND OF THE INVENTION

1. Field of the Invention

This invention relates to surgical instrumentation and more particularly to an instrument for use with an image-directed apparatus to perform an excisional biopsy, for example, of a lesion in a patient's breast. The invention and associated method relate to a manner in which biopsy tissue may be excised and extracted through a minimally invasive incision.

2. Description of Prior Art

It often is necessary to biopsy tissue from the interior of the body for diagnostic purposes. For example, when a physician discovers a suspicious breast lesion, a biopsy typically is performed on a small tissue sample to determine whether to remove the lesion or to perform another more invasive surgery. It remains common practice to use an open surgical approach to recover a tissue sample for biopsy purposes. Such an open excisional biopsy causes trauma and may leave undesirable scarring.

In many cases, a needle biopsy approach is employed. A "fine needle aspiration" approach utilizes a hollow 22 gauge needle wherein a small amount of tissue may be aspirated into the needle bore which then may be biopsied. Alternatively, a small core of tissue may be sampled with a "true-cut" or "quick-cut" needle in which an 18 gauge hollow needle with a sharpened tip reciprocates over a notched stylet. The elongate notch in the stylet collects a tissue core for biopsy purposes. Such needle-biopsy approaches cause little trauma but suffer from the disadvantage of recovering a only a small amount of tissue for biopsy purposes.

A recently developed approach is called a "large-core" stereotactic needle biopsy in which a 14 gauge hollow needle is employed together with an image-directed technology for digitally localizing the biopsy needle in relation to a breast lesion. To utilize the stereotactic needle apparatus, the patient lays prone on an operating platform that exposes and holds the breast in a stationary position below the platform. An x-ray stereo imaging unit is mounted below the platform and displays a stereo image of the lesion on a video monitor. A "large-core" needle assembly is mounted on a traveling arm below the platform and may be positioned in three axes by digital coordination with the stereo x-ray images. The large-core needle employs a 14 gauge hollow needle that reciprocates over a notched stylet similar to above-described "true-cut" needle. After the needle tip is digitally positioned just outside the breast, a double spring-loaded needle first projects the stylet through the lesion and then instantly projects the needle over the notched stylet to excise tissue within the notch in the stylet. The principal advantage of the stereotactic needle biopsy over other needle biopsy approaches is that the image-directed apparatus insures that tissue is excised from the exact site of the lesion. The 14 gauge needle also recovers a larger tissue sample than other needle biopsy approaches. Also, such a stereotactic needle biopsy causes little trauma because of the small diameter of the needle.

The stereotactic needle approach still does not recover a large tissue sample. Even in repeated cycles of insertion and withdrawal, 5 to 6 cycles being typical, the 14 gauge stereotactic needle can excise and extract only a small portion of a suspect lesion. In contrast, in an open excisional biopsy, the entire lesion may be removed. There is therefore a need for new instruments and methods for excising and extracting biopsy tissue from the interior of the body through a minimally invasive incision, and particularly for performing an excisional biopsy on a breast lesion through a needle incision utilizing a stereo image-directed apparatus to digitally localize the excision.

SUMMARY OF THE INVENTION

In general, the instrument and method in accordance with the present invention are utilized to excise and extract tissue from the interior of the body through a minimally invasive needle incision. The instrument is adapted for use with a stereotactic needle apparatus to precisely direct the tip of the needle assembly to the site of the lesion.

The instrument incorporates a disposable flex-blade needle cutter including:

(a) a hollow sleeve with a needle tip incorporating flexible rotatable blades that are movable between a first position in which the blades are contracted relative to the needle shaft for piercing into a patient's body and a second position in which the flexors are expanded in an arc outward relative to the needle shaft for excising tissue, (b) a blade-flexing mechanism for flexing the blades between the first and second positions;

(c) a rotation mechanism for rotating the flexors;

(d) an infusion channel within the hollow sleeve for supplying saline solution to the region of the flexors;

(e) an aspiration channel associated with the flexors for extracting fluids and excised tissue; and (f) a needle insertion mechanism for piercing the needle tip into tissue.

In using the flex-blade needle to remove a breast lesion, the surgeon locks the needle in an actuator incorporating actuation mechanisms, including a blade flexing mechanism, a blade rotation mechanism, a needle insertion mechanism, a saline infusion source and an aspiration source. The patient is positioned on a stereotactic needle apparatus. The actuator body then is fitted to the traveling arm of the stereotactic needle apparatus. The physician employs conventional digital imaging technology to direct the tip of the needle to the correct "x", "y" and "z" coordinates just exterior to the skin of the breast. The surgeon then selects a pre-programmed actuation cycle on a controller for the particular diameter of the needle and the dimensions of the tissue to be excised and extracted. The controller in sequence advances the needle tip with the flexors in the contracted position into the breast to the site of the lesion and then rotates and simultaneously flexes the flexors to the expanded position from the contracted position, thus incising tissue. At the same time, saline solution is infused into the region of the rotating flexors through the infusion channel while an aspiration source aspirates the excised tissue mixed with the saline through the separate aspiration channel. The extracted tissue is collected in a filter in a tissue-sampler. The controller then automatically returns the flexors to the contracted position and withdraws the needle from the breast.

In general, the present invention provides an instrument and method for excising and extracting tissue from the interior of the body (not just the breast) through a small diameter needle. The transverse sectional dimension of the excised tissue is advantageously large in relation to sectional dimension of needle shaft through which the tissue is extracted.

The present invention provides an instrument and method that cooperates with a stereotactic needle apparatus to digitally localize the excisional biopsy.

DESCRIPTION OF PREFERRED
EMBODIMENTS OF THE INVENTION

Figure 1:
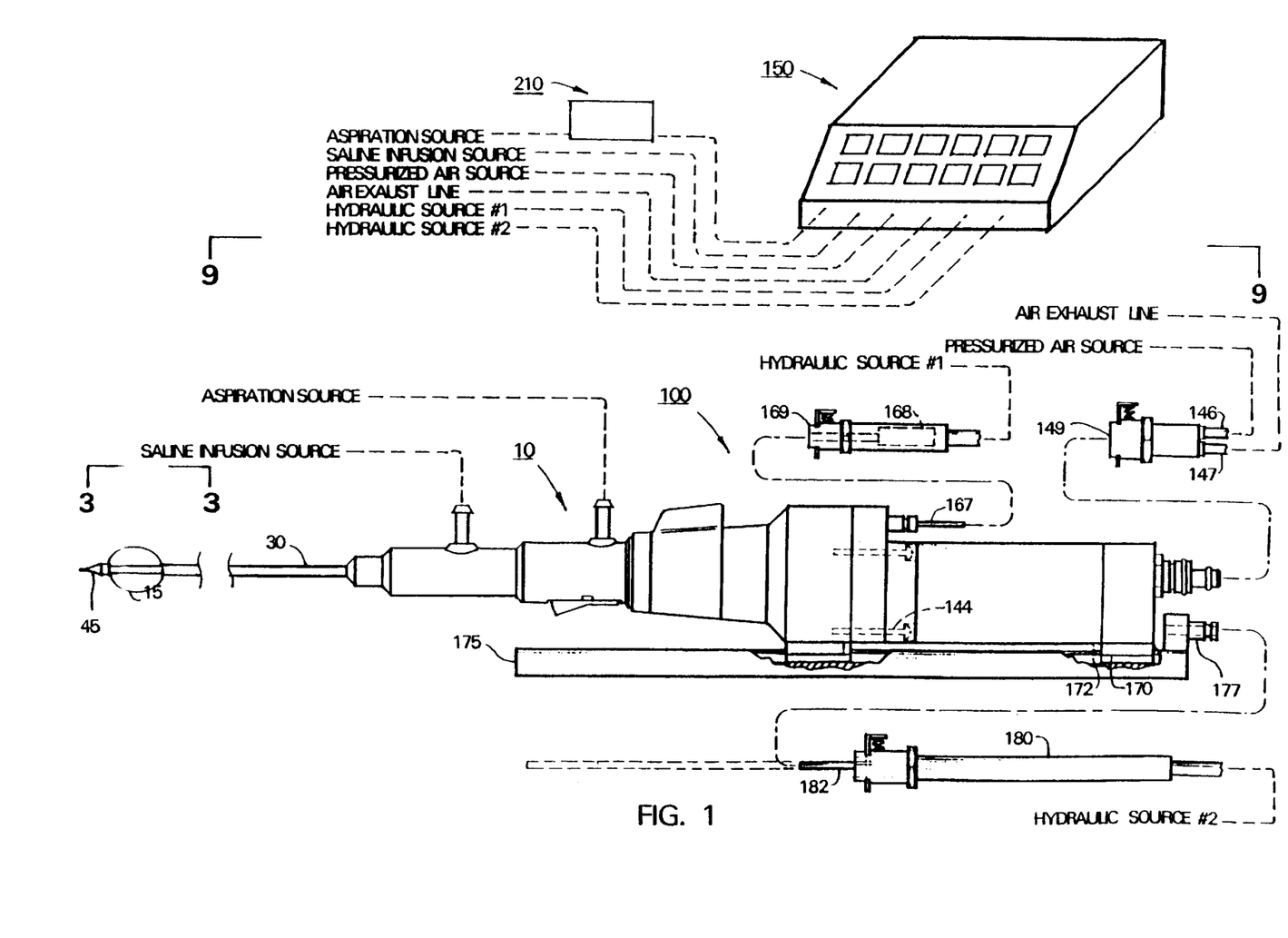
FIG. 1 is an elevational view of the present invention with the flex-blades of the needle in a flexed position.

By way of example, FIG. 1 illustrates a excisional needle biopsy device or instrument 5 in accordance with the present invention. Instrument 5 is adapted for use with a conventional stereotactic needle apparatus, for example, a Model DSM unit (Digital Spot Mammography) made by Lorad, Inc. of Danbury, Mass.

Figures 2, 3, 4:
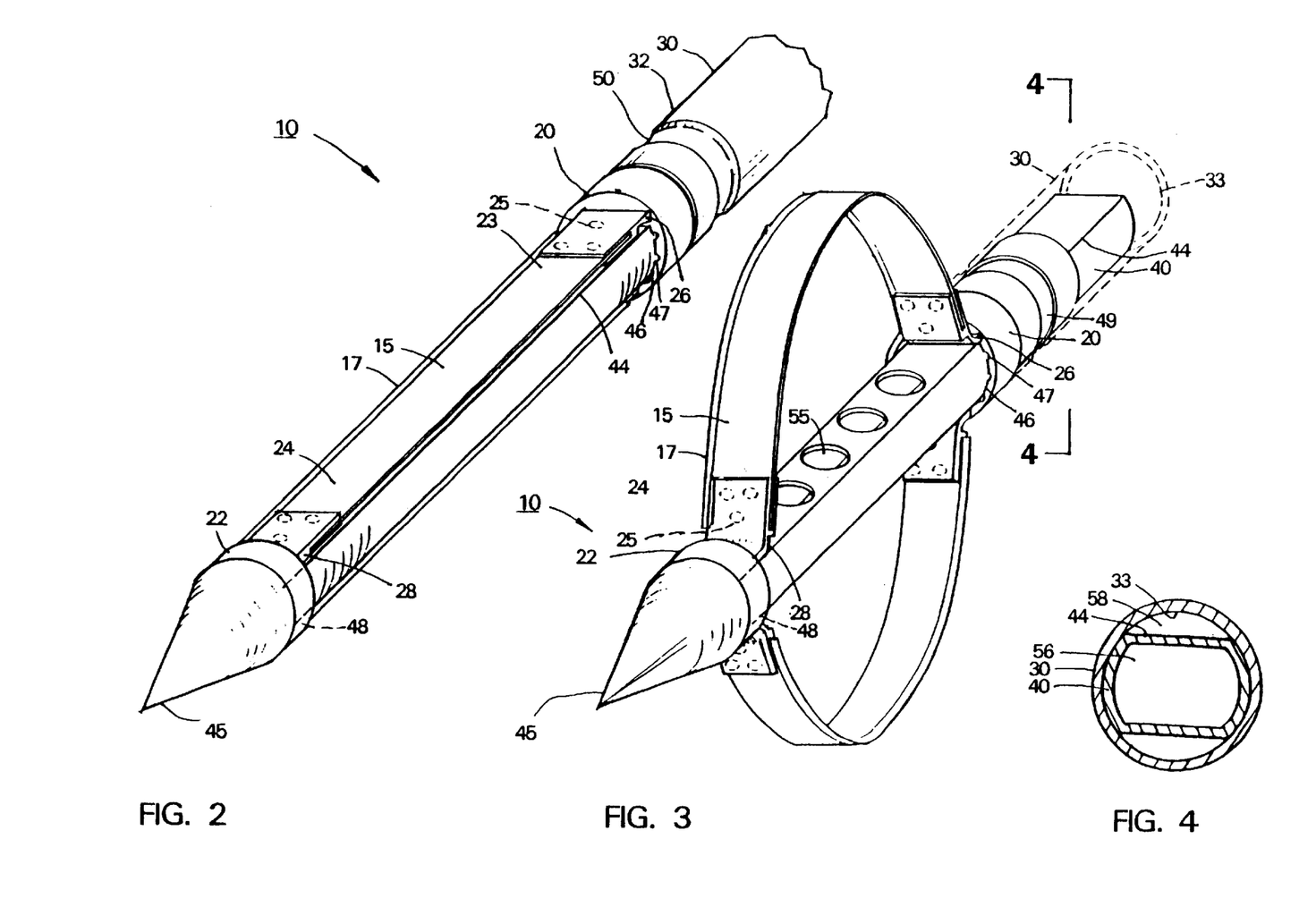
FIG. 2 is an enlarged axionometric view of the distal end of the flex-blade needle of the instrument of FIG. 1.
FIG. 3 is an enlarged axionometric view of the flex-blade needle of the instrument of FIG. 1 taken along line 3—3 of FIG. 1.
FIG. 4 is a transverse sectional view of the flex-blade needle of FIG. 3 taken along line 4—4 of FIG. 3.

Instrument 5 includes a disposable flex-blade cutter sub-assembly 10 (see FIG. 1). FIGS. 2–3 are axionometric views of the distal tip of flex-blade cutter 10 in alternative positions. In FIG. 2. flex-blade cutter 10 is illustrated with flexible blades or flexors 15 in a contracted or first position as when cutter 10 is configured for axial piercing into a patient's body. In FIG. 3, cutter 10 is depicted with flexors 15 in an expanded or second position as when the cutter is rotating at high speed to excise and extract tissue from a toroidal-shaped region. Flexors 15 are fabricated from any suitable material such as stainless steel ribbon having a thickness ranging e.g. from 0.002" to 0.015" and width ranging e.g. from 0.020" to 0.120" depending on the desired flexing characteristics and the dimensions of tissue to be excised (these dimensions are not limiting). For example, flexors 15 may be made of proprietary type UHB Stainless AEB-L by Uddeholm Corporation of Portland, Oreg. Each flexor is sharpened on one blade edge 17 or may be sharpened on both edges.

Still referring to FIGS. 2–3, the ends of flexors 15 are attached to proximal and distal hinge members respectively 20 and 22, that are made of any suitable resilient plastic material, for example Nylon or Delrin. The hinge members 20, 22 are injection-molded and grip the proximal and distal flexors ends respectively 23 and 24, through perforations 25 in the flexors. Resilient proximal and distal hinge portions respectively 26 and 28, have a thin cross-sections to attain suitable flexibility.

Outer sleeve 30 with proximal and distal ends respectively 31 (see FIG. 5) and 32, is fabricated from a thin-walled hollow tubular member, preferably stainless steel. Outer sleeve 30 is approximately 150 mm. in length (not limiting) and may be manufactured is various external diameters, for example 1 mm. to 5 mm. (not limiting). Bore 33 ill outer sleeve 30 is dimensioned to accommodate the rotation of rotator sleeve 40.

Rotator sleeve 40 has swaged flat regions 44 on two diametrically opposed sides, best illustrated in FIGS. 3–4. Sharp needle tip 45 is fixed to the distal end of rotator sleeve 40. Flat-sided bore 46 in proximal hinge member 20 is dimensioned to slide axially over swaged flats 44 but resist rotation around the swaged flats. Longitudinal grooves 47 provide a fluid channel between proximal hinge 20 and sleeve 40. Similar bore 48 in distal hinge member 22 is dimensioned to press fit over swaged flats 44 thereby resisting rotation around rotator sleeve 40. Annular groove 49 in the reduced diameter proximal shank of proximal hinge member 20 cooperates with indentation 50 in outer sleeve 30 in a slip-type fit to allow hinge member 20 to rotate relative to outer sleeve 30. Apertures 55 in rotator sleeve 40 in the region of flexors 15 communicate with interior bore or aspiration lumen 56 in sleeve 40. In the transverse sectional view of FIG. 4, it can be seen that a space exists between the outer surface of swaged flats 44 and bore 33 of outer sleeve 30 to provide infusion channel 58.

FIGS. 5–8 depict various views of cutter 10 with a component part disassembled to explain the manner in which flexors 15 are flexed between the first (contracted) position of FIG. 2 and second (expanded) position shown in FIG. 3.

Figure 5:
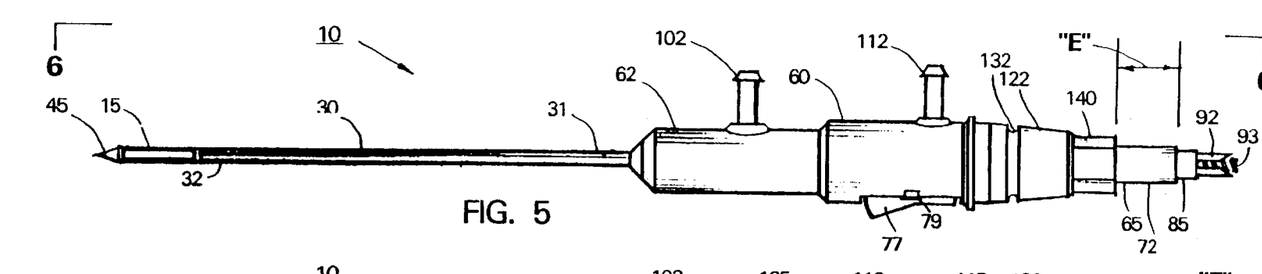
FIG. 5 is an elevational view of a cutter assembly with flex-blades in a first position for axial penetration of tissue.
Figure 6:
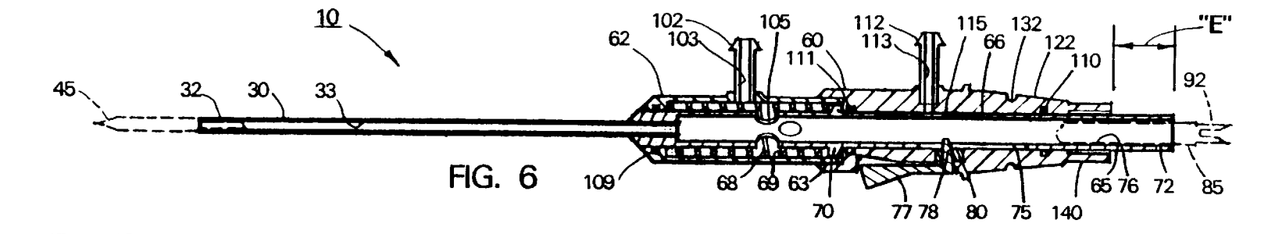
FIG. 6 is a longitudinal sectional view of the cutter assembly of FIG. 5 taken along line 6—6 of FIG. 5 rotated 90°.

Referring to FIGS. 5–6, cutter 10 has a body that includes a main housing 60 and a spring housing 62 that are generally cylindrical in shape and are made e.g. of injection-molded plastic. Spring housing 62 is fixed with adhesives or other suitable means into a receiving bore 63 in main housing 60.

Figure 8:
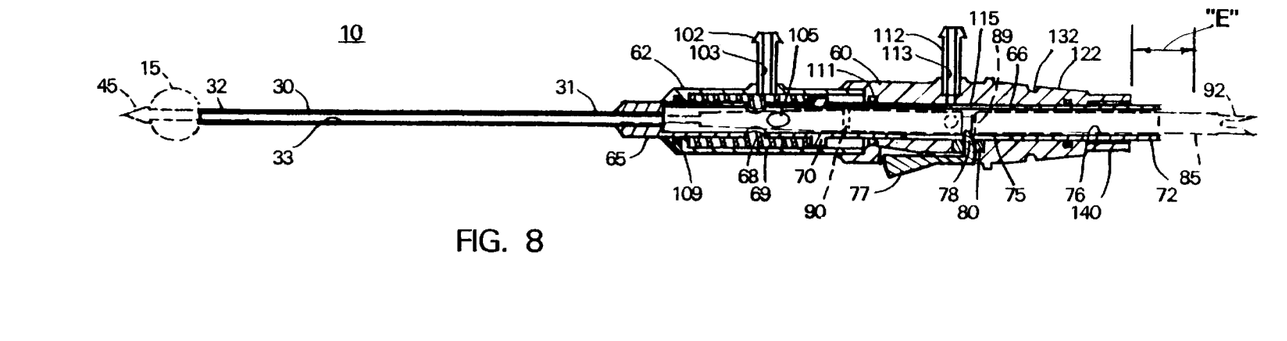
FIG. 8 is a longitudinal sectional view of the cutter assembly similar to FIG. 6 with the flex-blades in second position for excising tissue.

Referring to FIG. 6, actuator sleeve 65 for actuating flexors 15 is dimensioned to reciprocate in bore 66 that extends through main end spring housings, 60 and 62. The proximal end of outer sleeve 30 is fixed in the distal end of actuator sleeve 65. Compression spring 68 is captured in spring bore 69 and engages flange 70 of actuator sleeve 65 to urge the sleeve to its proximalmost position which in turn causes outer sleeve 30 in cooperation with proximal hinge 20 to maintain the flexors in the first (contracted) position (see FIG. 2). In FIG. 8, actuator sleeve 65 is shown in an alternative position partially projected outward (distally) with spring 68 being partially compressed which in turn causes the distal sliding of outer sleeve 30 to flex the flexors. Referring to FIGS. 5–6 and 8, it can be seen that proximal end 72 of actuator sleeve 65 extends proximally from main housing 60 a distance referred to as extension distance "E" and a distal force applied to proximal end 72 will cause flexors 15 to flex.

A mechanism is provided to allow actuator sleeve 65 to slide axially but prevent the sleeve from rotating. As shown in FIG. 6, longitudinal groove 75 in actuator sleeve 65 extends into bore 76 in the sleeve. Slot 75 is aligned with latch 77 and the inwardly projecting arm 78 of the latch extend through slot 75 inward toward the axis of actuator sleeve 65. Latch 77 has resilient pivot arms 79 (see FIG. 1) that snap fit into main housing 60 and yieldably maintain latch 77 in the latched position shown in FIGS. 5–6 and 8. Projecting arm 78 extends through a fluid-tight flexible seal 80 in main housing 60 into slot 75.

Figure 7:
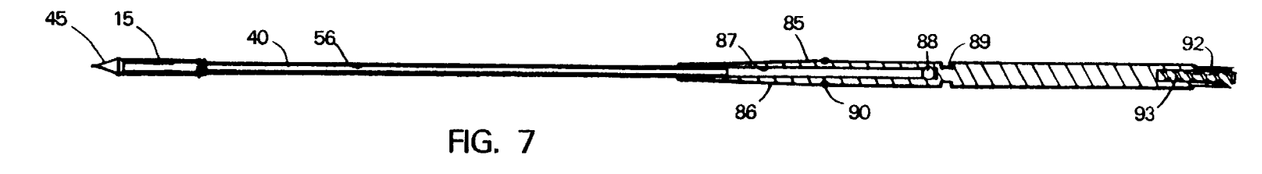
FIG. 7 is a sectional view of a component of the cutter assembly of FIG. 5.

Referring to FIG. 7, rotator sleeve 40 and more particularly its proximal end is fixed to e.g. plastic rotator stem 85. Stem 85 with distal tapered region 86 is dimensioned to freely rotate in bore 76 of actuation sleeve 65. Bore or aspiration lumen 56 in sleeve 40 is aligned with counter bore 87 in stem 85. Diametrically opposed apertures 88 in stem 85 communicate with counterbore 87. Rotator sleeve 40 and stem 85 are maintained in a fixed axial position relative to cutter 10 as rotator stem 85 rotates yet still allowing actuator sleeve 65 to reciprocate over the stem. Annular groove 89 in stem 85 is engaged by the tip of projecting arm 78 of latch 77, which allows the stem 85 to rotate but not move axially.

The proximal end of rotator stem 85 includes a female spline-receiving fitting 92 (see FIGS. 5 and 7). The spline fitting 92 is adapted to engage a cooperating fitting in a motor further described below. Compression spring 93 in the proximal end of stem 85 urges the stem and cutter 10 from engagement with the motor and actuator 100 further described below.

Fluids may be infused under pressure, for example saline solution, to the region of flexors 15, by a conventional operating room (OR) saline source connected to Luer-type fitting 102 in cutter 10 (see FIG. 1). Referring to FIG. 8, fluid passageway 103 in fitting 102 communicates with the internal spring bore 69 in spring housing 62. Fluid in spring bore 69 may flow freely through inflow apertures 105 into bore 76 in actuator sleeve 65. Once fluid is under pressure within the actuator sleeve bore 76, it may flow distally over taper 86 in stem 85 and into infusion channels 58 within bore 33 to the region of proximal hinge member 20 and thereafter though longitudinal grooves 47 in flat-sided bore 46 of hinge 20 to escape to the region of the flexors. Once fluid is under pressure within actuator sleeve bore 76, it is prevented from flowing in the proximal direction by "O"-ring 90 mounted around rotator stem 85 in actuator sleeve bore 76, as shown in phantom view in FIG. 8. Fluid in spring bore 69 is prevented from flowing around the outer surface of actuator sleeve 65 by distal "O"-ring 109 and medial "O"-ring 111. Thus, fluid infusion to the flexors may occur when actuator sleeve 65 is in either a retracted or projected position.

Fluids may be aspirated from the region of flexors 15 by a conventional OR suction or aspiration source connected to Luer-type fitting 112 in main housing 60. Referring to FIG. 6, fluid passageway 113 communicates with the bore 66 in main housing 60. Suction pressure in bore 66 flows through longitudinal slot 115 into bore 76 in actuator sleeve 65. Once suction pressure is within the actuator sleeve bore, the suction communicates with apertures 88 in rotator stem 85 as the stem rotates. Apertures 88 allow suction pressure to flow through counterbore 87 into aligned bore or aspiration lumen 56 in rotator sleeve 40. Such suction pressure then aspirates fluids from the region of the flexors though apertures 55 in the rotator sleeve (see FIG. 3). Suction pressure within bore 66 is prevented from escaping around the outer surface of actuator sleeve 65 by medial "O"-ring 111 and proximal "O"-ring 110. Also, suction pressure does not escape around latch projecting arm 78 because of fluid-tight seal 80. Thus, aspiration pressure to the region of flexors 15 is provided when actuator sleeve 65 is any position, either retracted or projected (see FIGS. 6 and 8).

Actuator 100 (see FIGS. 9–10) provides various mechanisms for mechanizing cutter 10, and more specifically reciprocates actuator sleeve 65 to flex the flexors, rotates the flexors and means for axially moves cutter 10 to pierce through tissue into the interior of the body. Actuator 100 includes four housing components ("A", "B", "C" and "D") that are axially aligned and made of metal or plastic.

Figure 9:
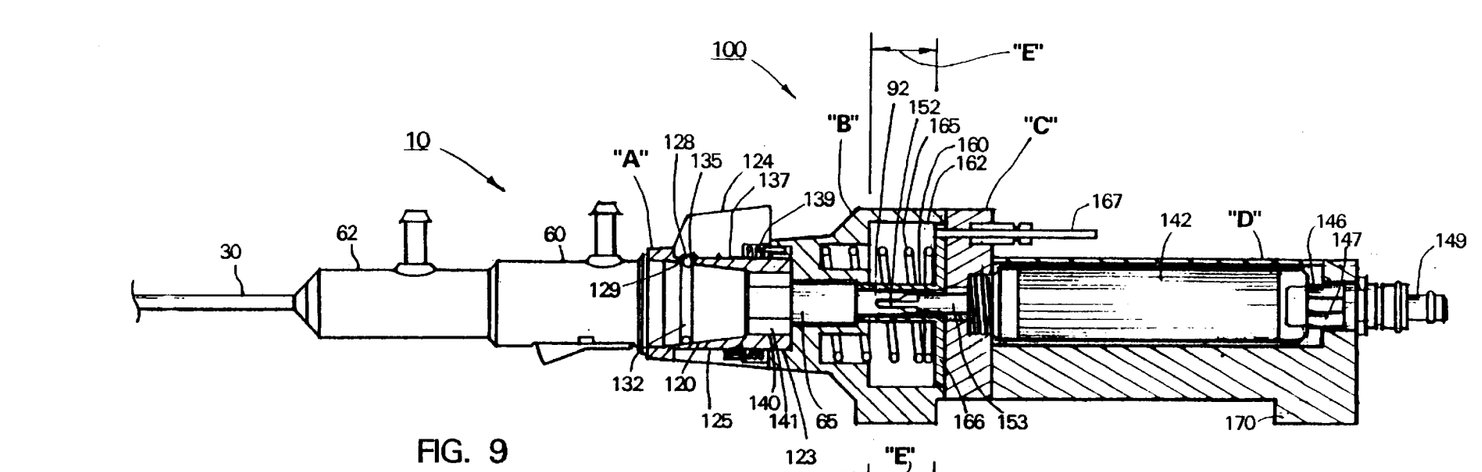
FIG. 9 is a partial sectional view of the actuator of FIG. 1 taken along line 9—9 of FIG. 1 rotated 90°.

Actuator 100 includes a latch for releasably locking cutter 10 into the actuator. As seen in FIG. 9, housing "A" at the distal end of actuator 100 has a female conical-shaped bore 120 that receives the conical-shaped proximal end 122 of main housing 60 of cutter 10. Housing "A" is fixed in counterbore 123 in housing "B". Locking collar 124 is captured between housings "A" and "B" and rotates around cylindrical portion 125 of housing "A". The latch includes a round bearing 128 projecting partially though partial radial bore 129 to engage annular groove 132 in main housing 60. Locking collar 124 is configured with a variable depth groove 135 in its inner bore 137 that pushes bearing 128 radially inward to a locking position as shown in FIG. 9. Torsion spring 139 urges locking collar to rotate to the locking position. By rotating locking collar 124 and overcoming the force of torsion spring 139, the radial depth of groove 135 increases, thus permitting bearing 128 to be displaced outwardly to release its engagement with annular groove 132 and permitting cutter 10 to be withdrawn distally.

Male hex-configured region 140 of main housing 60 fits into female hex-receiving form 141 in actuator 100 (see FIG. 10) to prevent rotation of the cutter 10 relative to actuator 100.

Figure 10:
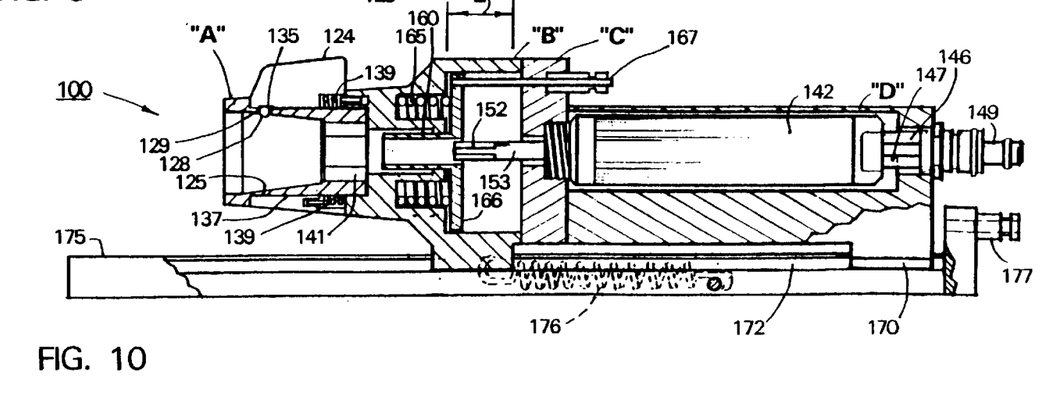
FIG. 10 is a partial sectional view of actuator of FIG. 9 in an alternative position.

A mechanism is provided for rotating rotator sleeve 40 and rotator stem 85 thus rotating flexors 15. Referring to FIGS. 9–10, the rotation mechanism is motor 142 such as commercially available from Micro Motors of Santa Ana, Calif., for example, model number MMR-0700 or MMR-0014. The distal end of motor 142 has male threads 143 that are fitted into housing "C". Housings "B", "C" and "D" are fixed together by screws 144 (see FIG. 1) or other suitable fasteners. Motor 142 is a turbine that is rotated by pressurized air supply line 146 and cooperating air exhaust line 147 that are fixed to a quick disconnect coupling 149, for example, similar to part K-212010 from Small Parts, Inc., of Miami Lakes, Fla. The instrument alternatively may be powered by an electric motor. The pressurized air supply is fed through controller 150 (FIG. 1) which may include an electronic feedback circuit (not shown) capable of sensing the load on rotating flexors 15 and rotator sleeve 40 as tissue is excised to maintain optimum torque and rotational speed within defined parameters.

A four-sided spline 152 at the distal end of motor shaft 153 engages female spline-receiving fitting 92 in the proximal end of rotator stem 85 (see FIGS. 5 and 7).

An actuator is provided for flexing the flexors 15 to the second (expanded) position as shown in FIG. 3 from the first (contracted) position as shown in FIG. 2. The actuator includes reciprocating plunger 160 that pushes on proximal end 72 of actuator sleeve 65 as plunger 160 moves to and fro in cylindrical plunger chamber 162. Compression spring 165 engages flange 166 and yieldably maintains plunger 160 in its proximalmost position shown in FIG. 9 with extension distance "E" again indicating a range of axial travel. In FIG. 10, plunger 160 is illustrated in its distalmost projected position. To move plunger 160 to its second position from its first position, pin 167 which is fixed in flange 166 may be pushed distally by a piston 168 within a quick-disconnect hydraulic fitting 169 (see FIG. 1).

A needle insertion mechanism is provided for piercing and withdrawing the distal end of cutter 10 with respect to a patient's body. Referring to FIGS. 9–10, actuator 100 has feet 170 that slidably engage longitudinal tracks 172 in guide 175. Guide 175 shown in FIG. 10 allows for travel of approximately 2 to 4 inches (not limiting). Actuator 100 is yieldably maintained in its proximalmost sliding position within tracks 172 by extension spring 176 shown in phantom view in FIG. 10. Guide 175 has fitting 177 that cooperates with quick-disconnect hydraulic piston fitting 180 (see FIG. 1). Referring to FIG. 1, piston 182 is illustrated in a withdrawn position with a phantom view of its projected position. To move actuator 100 to its projected position from its withdrawn position, controller 150 uses a hydraulic line to actuate piston 182 thus making actuator 100 slide distally in tracks 172. Guide 175 is adapted for locking in the traveling arm of the stereotactic needle assembly by thumbscrews or other suitable means.

A controller sequences the actuation of the projecting mechanism, the rotation mechanism and the blade-flexing mechanism as well as the saline infusion and aspiration. Controller 150 incorporates integrated circuitry to automatically actuate the various actuation mechanisms in pre-programmed cycles. The cycles differ for each different diameter of cutter 10.

A mechanism is are also provided for collecting extracted tissue. Referring to FIG. 1, the aspiration source is provided with a tissue filter subassembly 210 shown schematically. A conventional autoclavable stainless steel filter with replaceable filter membranes may be provided to separate tissue from infused saline solution, and may be part no. Q-202025 from Small Parts, Inc., of Miami Lakes, Fla.

Operation and use of instrument 5 for excising tissue from a lesion in a breast is briefly described as follows. The surgeon mounts actuator 100 on the traveling arm of a conventional stereotactic needle apparatus. The actuation lines are connected between actuator 100 and controller 150.

A patient is prepared with suitable local anesthesia and positioned on the platform of the stereotactic needle apparatus. The surgeon then fits a disposable cutter 10 into actuator 100. The locking collar 124 is rotated overcoming the force exerted by torsion spring 139 thus permitting bearing 138 to be displaced radially outward. The proximal end of cutter 10 is introduced into conical bore 120 and the release of collar 124 causes bearing 138 to project radially inward into annular groove 132 to lock cutter 10 in place. The cooperating hex-shapes 140 and 141 of cutter 10 and actuator 100 angularly lock the cutter relative to the actuator.

The surgeon then uses the digital controls on the stereotactic needle apparatus to direct tip 45 of cutter 10 to a position aligned with the lesion but still about 5 mm. outside the patient's skin on the "z" axis. The surgeon then nicks the skin with a scalpel. The surgeon then selects a pre-programmed actuation cycle on controller 150 for the particular diameter of cutter 10 and the dimensions of the tissue to be excised. Upon pressing a button to actuate a cycle, controller 150 first moves actuator 100 distally to pierce needle tip 45 directly through the breast lesion as can be seen on the video monitor. Then, the controller simultaneously and sequentially rotates flexors 15, flexes the flexors to the second (expanded) position from the first (contracted) position and infuses flexors 15 with saline fluid which flows through infusion channel 58 between outer sleeve 30 and rotator sleeve 40. Also at the same time, the aspiration source aspirates saline fluids mixed with excised tissue through apertures 55 in rotator sleeve 40 inward of flexors 15 and thereafter through aspiration lumen 56. Aspirated tissue is separated from saline solution fluid within tissue filter subassembly 210. The surgeon may view the pre-programmed actuation cycle on the video monitor. The actuation cycle concludes with controller 150 automatically withdrawing needle tip 45 from the breast.

Figures 11, 12, 13, 14:
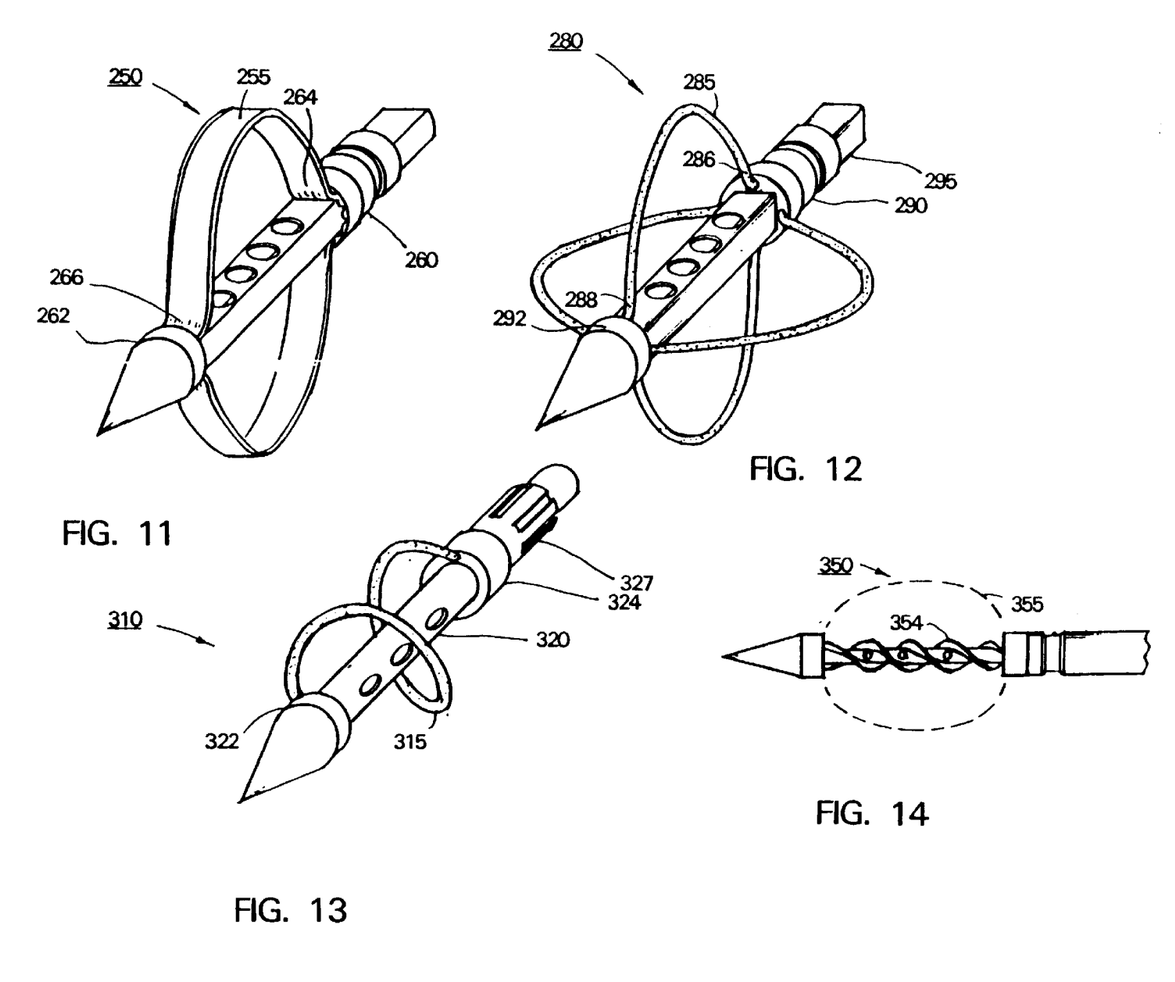
FIG. 11 is an axionometric view of an alternative embodiment of a flex-blade needle.
FIG. 12 is an axionometric view of an alternative embodiment of a flex-blade needle.
FIG. 13 is an axionometric view of an alternative embodiment of a flex-blade needle.
FIG. 14 is an elevational view of an alternative embodiment of a flex-blade cutter.

Referring to FIG. 11, an alternative embodiment of a flex-blade cutter is shown in which cutter 250 has flexors 255 and proximal and distal hinge components 260 and 262 made of a unitary injection-molded plastic member. Proximal and distal hinge elements 264 and 266 are thin and flexible in cross section to provide suitable flexing characteristics. A resilient plastic such as Delrin is suitable for a unitary flex-blade cutter and may still have a sufficiently sharp edge for a single use to excise tissue.

Referring to FIG. 12, an alternative embodiment of a flex-blade cutter for a small diameter cutter is shown in which cutter 280 has a plurality of flexors 285 made of flexible wire such as stainless steel. The proximal and distal regions 286 and 288 of each wire comprises a hinge. The wires are fixed in proximal and distal blade spindles 290 and 292, for example as inserts in an injection molding process, and the assembly cooperates with rotator sleeve 295 as described in the previous embodiment. The wires may range in diameter from 0.005" to 0.050" (not limiting) depending on the diameter of cutter 280. To enhance the excising ability of a cutter with such wire flexors 285, the flexors may have an abrasive finish, such as a passivated or sandblasted finish, to enhance its ability to excise tissue as it rotates.

Referring still to FIG. 12, flexors 285 may also be fabricated out of a very flexible plastic material such as a plastic monofilament and be suitable for excising tissue. In an embodiment with a very flexible flexor 285, the blade flexing mechanism to move the flexors to the second (expanded) position from the first (contracted) position may include only the centrifugal force on rotator sleeve 295 which will cause the flexors to bend radially outward as depicted in FIG. 12 under high speed rotation which will overcome pressure of tissue on the flexors. In any cutter employing such centrifugal force for blade-flexing, the spring 68 (see e.g., FIG. 6) in the cutter housing will move the flexors to the first (contracted) position from the second (expanded) position after rotation of sleeve 295 is slowed and then stopped.

Referring to FIG. 13, an alternative embodiment of a rotatable flex-blade cutter is shown in which cutter 310 has a single flexor 315 made of a flexible wire is at least partially helically wrapped around rotator sleeve 320. The flexor 315 is maintained in either a contracted or expanded position by counter-rotating distal spindle 322 relative to proximal spindle 324. Splines 327 are adapted to engage an outer sleeve (not shown) that in concentrically mounted over inner sleeve 320. In any cutter employing such a helically wrapped flexor 315, the flexor also may be flexed by centrifugal force on the rotator sleeve as described above. In any cutter with a helically wrapped flexor 315, the force or spring constant within the flexor itself may be utilized to move the flexor 315 to the first (contracted) position from the second (expanded) position after rotation of sleeve 320 is slowed and stopped.

Referring to FIG. 14, an alternative embodiment of a flex-blade cutter 350 in which the tissue aspiration mechanism includes an auger member 354 which rotates in cooperation with flexors 355 to draw excised tissue into the bore in sleeve 360.

It should be appreciated that all of the above-described embodiments of cutters may include a reciprocating external protective sleeve (not shown) to cover the flexors of the cutter in the first (contractor) position to facilitate piercing into tissue. Such an external sleeve then would slide proximally to expose the flexors and thereby permit the flexors to flex to the second (expanded) position.

Actuator 100 also may be employed to actuate a non-rotating embodiment of a needle-cutter 510 that is illustrated in FIGS. 15–18. This embodiment is adapted to excise tissue with a reciprocating needle sleeve only.

Figure 15:
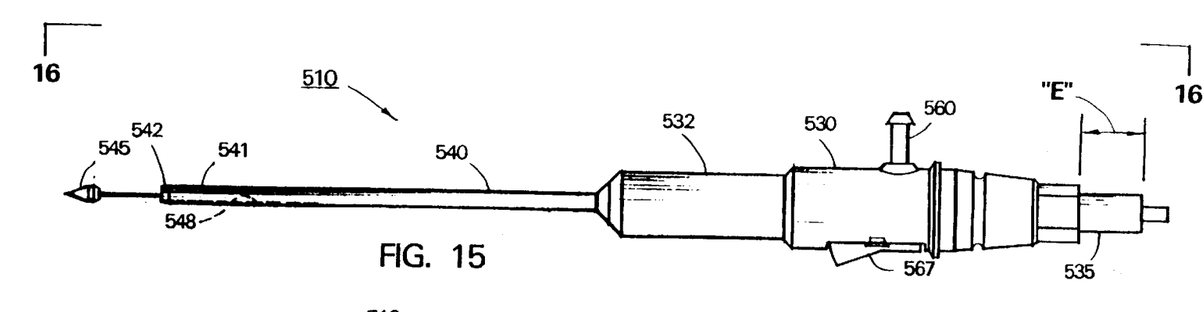
FIG. 15 is an elevational view of an alternative embodiment of a cutter assembly in a first position.
Figures 16, 17:
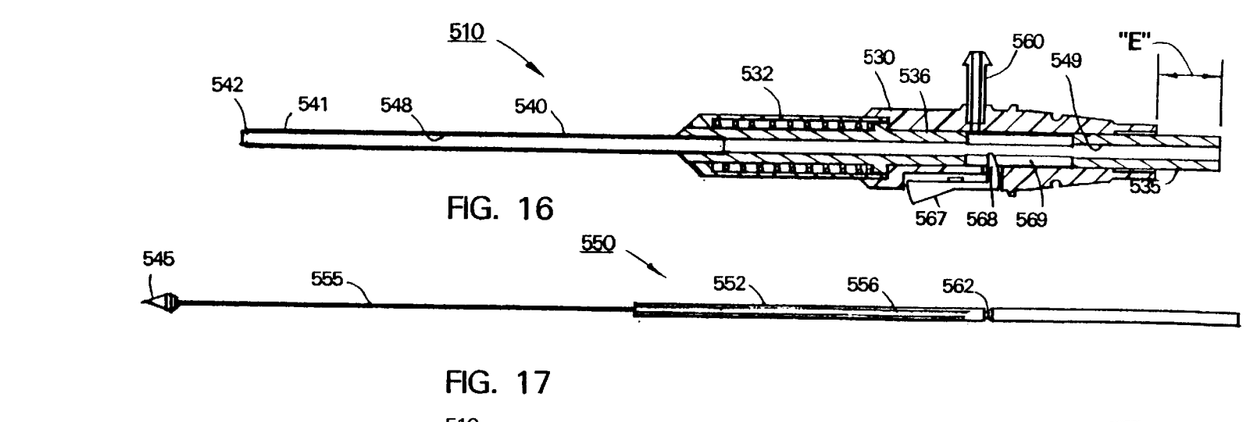
FIG. 16 is a longitudinal sectional view of the cutter assembly of FIG. 15 taken along line 16—16 of FIG. 15 rotated 90°.
FIG. 17 is an elevational view of a component of the cutter assembly of FIG. 15.

In FIGS. 15–16, it can be seen that main housing 530 and spring housing 532 are similar to the above-described embodiment. The actuator sleeve 535 functions as in the previous embodiment and reciprocates through bore 536 in the spring and main housings, 530 and 532. Actuator 100 is capable of reciprocating actuator sleeve 535 a distance again referred to as extension distance "E".

Referring to FIG. 15, excising sleeve 540 is fabricated from a thin-walled hollow stainless steel tube. The distal end 541 of excising sleeve 540 is ground and honed circumferentially as a cylindrical cutting edge 542 to excise tissue as the cutting edge 541 is projected in a distal direction over needle tip 545. The excising sleeve 540 is approximately 200 mm. in length and may be manufactured in various external diameters, for example 1 mm. to 5 mm. (not limiting). Bore or tissue-collecting lumen 548 in excising sleeve 540 collects excised tissue cores and is aligned with bore 549 extending through actuator sleeve 535.

Referring to FIG. 17, obturator 550 includes a shaft portion 552 and a piercing tip 545 fixed to wire 555, for example by laser welding, and is dimensioned to slide in bore 549 in actuator sleeve 535. Shallow longitudinal grooves 556 in the outer surface of shaft 552 optionally to allow aspirated air to travel from the distal end of lumen 548 to aspiration port 560. Latch arm 567 with projecting tip 568 extends through slot 569 into bore 549 and engages annular notch 562 in shaft 552 to maintain obturator 550 in a fixed position relative to main housing 530 thus allowing actuator sleeve 535 to freely reciprocate.

Figure 18:
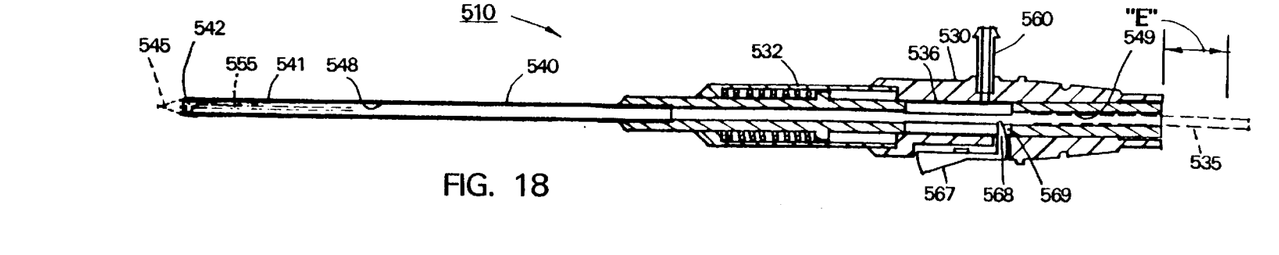
FIG. 18 is a longitudinal sectional view of the cutter assembly similar to FIG. 16 in a second position.

The operation of reciprocating needle-cutter 510 employs the above-described needle insertion mechanism to pierce the needle tip into a breast lesion with the needle tip 545 held in registration with the excising sleeve 540 as shown in FIG. 18. The reciprocating mechanism within actuator 100 then is used to move the excising sleeve proximally (see FIG. 15) and then distally (see FIG. 18) to excise a large core of tissue. Such a tissue coring cycle may be repeated. The tissue core can be recovered from bore 549 by releasing latch 567 an pulling obturator 550 proximally from main housing 530.

Although the invention has been described in connection with a breast biopsy procedure, it should be appreciated that the device and method of the invention can be used in other minimally invasion tissue excising procedures. For example, the device can be used to excise lesions within muscles or organs such as the liver. It should also be appreciated that the needle assemblies may be fitted to a hand held motor housing with a pistol grip to manually excise and extract tissue from the interior of a body region or organ and be within the scope of the invention.

I claim:

1. An excisional biopsy needle for use in excising tissue from the interior of a body, comprising:

(a) a sleeve defining an interior bore extending therethrough along a central axis;

(b) a stylet dimensioned to reciprocate in said interior bore, wherein a distal portion of the stylet comprises a sharp tip having a cross-sectional dimension that fits closely in said interior bore and wherein medial and proximal portions of said stylet comprise a wire cutting element extending along said axis, the wire cutting element having a lesser diameter than the cross-sectional dimension of said sharp tip and fitting loosely in said interior bore; and (c) a reciprocating structure operatively connected to the sleeve and the stylet, thereby reciprocating the sleeve relative to the stylet between a first position in which the tip of the stylet is disposed at the distal end of the sleeve and a second position in which the tip of the stylet is disposed distally beyond the distal end of the sleeve thus exposing the wire cutting element which in the second position has a transverse dimension greater than the transverse dimension of the sleeve.

2. The instrument of claim 1, wherein the distal end of the sleeve has a sharp edge.

3. The instrument of claim 1, wherein a diameter of said interior bore is constant along a length of said wire cutting element when said second sleeve is in said first position.

4. The instrument of claim 1, wherein medial and proximal portions of said stylet comprise a second wire cutting element extending along said axis, said second wire cutting element having a lesser diameter than the cross-sectional dimension of said sharp tip and fitting loosely in said interior bore.

5. The instrument of claim 1, wherein the wire cutting element has a diameter between 0.005 and 0.05 inches.

6. The instrument of claim 1, wherein the wire cutting element is formed from flexible plastic material.

7. The instrument of claim 1, wherein the stylet further comprises a second sleeve and wherein the wire cutting element and second sleeve are coupled to each other via a hinge.

8. The instrument of claim 7, wherein a portion of the wire cutting element is helically wrapped around the second sleeve.

* * * * *